United States Patent [19]

Weisman et al.

[11] Patent Number: 4,610,678
[45] Date of Patent: Sep. 9, 1986

[54] HIGH-DENSITY ABSORBENT STRUCTURES

[76] Inventors: Paul T. Weisman; Stephen A. Goldman, both of P.O. Box 39175, Cincinnati, Ohio 45247

[21] Appl. No.: 529,900

[22] Filed: Sep. 6, 1983

Related U.S. Application Data

[63] Continuation-in-part of Ser. No. 507,824, Jun. 24, 1983, abandoned, which is a continuation-in-part of Ser. No. 437,846, Mar. 10, 1983, abandoned.

[51] Int. Cl.$^4$ ............................................. A61F 13/16
[52] U.S. Cl. ...................................... 604/368; 604/379
[58] Field of Search ......................... 604/368, 379, 380

[56] References Cited

U.S. PATENT DOCUMENTS

| | | | |
|---|---|---|---|
| 2,750,944 | 6/1956 | Tollstrup | 128/290 |
| 3,070,095 | 12/1962 | Torr | 128/284 |
| 3,187,747 | 6/1965 | Burgeni | 128/156 |
| 3,241,553 | 3/1966 | Steiger | 128/156 |
| 3,344,789 | 10/1967 | Arnold et al. | 128/287 |
| 3,347,236 | 10/1967 | Torr | 128/284 |
| 3,381,688 | 5/1968 | Satas | 128/296 |
| 3,528,421 | 9/1970 | Vaillancourt et al. | 128/284 |
| 3,661,154 | 5/1972 | Torr | 128/284 |
| 3,669,103 | 6/1972 | Harper et al. | 128/156 |
| 3,670,731 | 6/1972 | Harmon | 128/284 |
| 3,731,686 | 5/1973 | Chatterjee | 128/285 |
| 3,783,872 | 1/1974 | King | 128/290 R |
| 3,888,257 | 6/1975 | Cook et al. | 128/296 |
| 3,901,236 | 8/1975 | Assarsson et al. | 128/284 |
| 3,971,379 | 7/1976 | Chatterjee | 128/285 |
| 4,055,180 | 10/1977 | Karami | 128/287 |
| 4,062,817 | 12/1977 | Westerman | 260/17.45 G |
| 4,076,663 | 2/1978 | Masuda et al. | 260/17.4 GC |
| 4,102,340 | 7/1978 | Mesek et al. | 128/287 |
| 4,103,062 | 7/1978 | Aberson et al. | 428/283 |
| 4,105,033 | 8/1978 | Chatterjee et al. | 128/285 |
| 4,208,459 | 6/1980 | Becker et al. | 604/368 |
| 4,212,302 | 7/1980 | Karami | 128/287 |
| 4,217,901 | 8/1980 | Bradstreet et al. | 128/290 R |
| 4,232,674 | 11/1980 | Melican | 128/287 |
| 4,235,237 | 11/1980 | Mesek et al. | 128/284 |
| 4,252,761 | 2/1981 | Schoggen et al. | 264/120 |
| 4,286,082 | 8/1981 | Tsubakimoto et al. | 526/240 |
| 4,327,728 | 5/1982 | Elias | 128/285 |
| 4,333,461 | 6/1982 | Muller | 128/284 |
| 4,333,462 | 6/1982 | Holtman et al. | 128/287 |
| 4,333,463 | 6/1982 | Holtman | 128/287 |
| 4,340,556 | 7/1982 | Ciencewicki | 604/368 |
| 4,354,487 | 10/1982 | Oczkowski et al. | 128/156 |
| 4,354,901 | 10/1982 | Kopolow et al. | 162/158 |
| 4,381,782 | 5/1983 | Mazurak et al. | 604/368 |
| 4,475,911 | 10/1984 | Gellert | 604/367 |
| 4,500,315 | 2/1985 | Pieniak et al. | 604/379 |

FOREIGN PATENT DOCUMENTS

| | | |
|---|---|---|
| 2293913 | 7/1976 | France . |
| 13409451 | 10/1976 | Japan . |
| 9904677 | 7/1977 | Japan . |
| 6563056 | 6/1981 | Japan . |
| 549213 | 11/1942 | United Kingdom . |
| 1406615 | 9/1975 | United Kingdom . |
| 1500559 | 2/1978 | United Kingdom . |
| 1548156 | 7/1979 | United Kingdom . |

OTHER PUBLICATIONS

Carus, "The Development and Uses of Superabsorbents in Incontinent Products", *Insight 80 Proceedings*, Nov. 19-21, 1980.

Buckeye Cellulose, Disclosure No. 15049, *Research Disclosure*, Oct. 1976, pp. 29-30.

Erickson et al; "Absorbent Laminate for Low Bulk, High Capacity Personal Care Products", *Insight 80 Proceedings*, Nov. 19-21, 1980.

*Primary Examiner*—Stephen C. Pellegrino
*Assistant Examiner*—S. E. Vinyard

[57] ABSTRACT

Absorbent structures comprising a mixture of hydrophilic fibers and discrete particles of a water insoluble hydrogel are disclosed. The fiber/hydrogel ratios range from about 30:70 to about 98:2. The absorbent structures have a density of from about 0.15 g/cm$^3$ to about 1 g/cm$^3$. The structures are flexible, and have superior absorption capacities for water and body fluids.

33 Claims, 1 Drawing Figure

U.S. Patent  Sep. 9, 1986  4,610,678
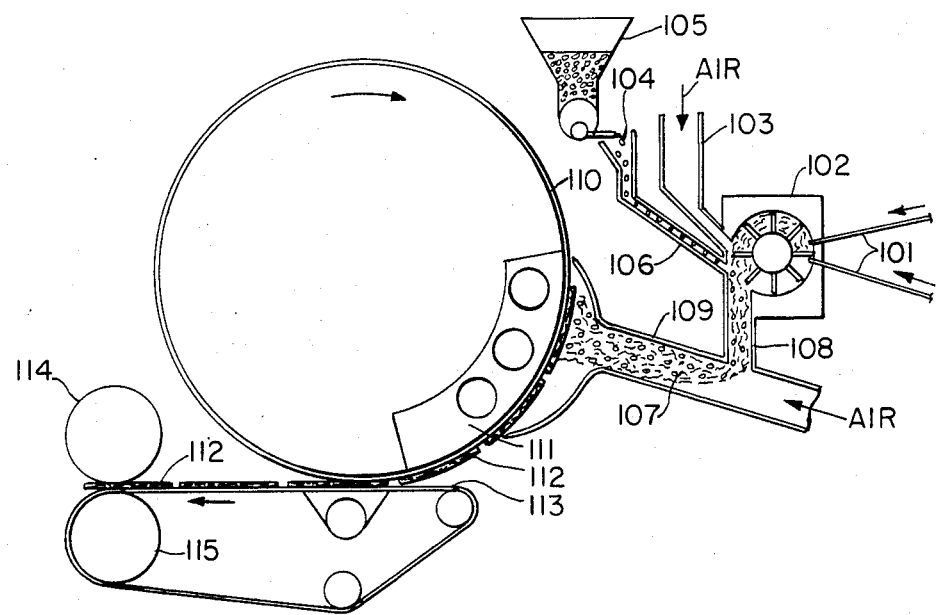

HIGH-DENSITY ABSORBENT STRUCTURES

The present application is a continuation-in-part of application Ser. No. 507,824 filed June 24, 1983, and now abandoned, which is a continuation-in-part of application Ser. No. 437,846 filed Mar. 10, 1983, and now abandoned.

TECHNICAL FIELD

This invention relates to flexible, substantially unbonded, absorbent structures comprising a mixture of hydrophilic fibers and discrete particles of a water-insoluble hydrogel. Flexible absorbent structures, generally non-woven sheets or fibrous webs, have the ability to absorb significant quantities of fluids like water and body exudates. They are used, for example, as disposable towels, facial tissues, toilet tissue, or as adsorbent cores in absorbent products like disposable diapers and sanitary napkins. Generally, such structures are made of inexpensive hydrophilic fibers, typically wood pulp fibers.

Water-insoluble hydrogels are polymeric materials which are capable of absorbing large quantities of water, typically more than 20 times their own weight. When first introduced, these materials were expected to generate a major breakthrough in the world of disposable absorbent consumer products (i.e. products like disposable diapers, sanitary napkins, incontinent pads, and the like). Yet, up to this day, no large-scale use of water-insoluble hydrogels in disposable absorbent products has taken place. The reason is that, in spite of the extremely high water absorption capacities of hydrogels, their performance when used in disposable absorbent products has been unacceptable.

One cause of the poor performance of hydrogels is a phenomenon called gel blocking. The term gel blocking describes a phenomenon that occurs when a hydrogel particle, film, fiber, etc. is wetted; the surface swells and inhibits liquid transmission to the interior. Wetting of the interior subsequently takes place via a very slow diffusion process. In practical terms this means that the absorption is much slower than discharge of fluid to be absorbed, and failure of a diaper or sanitary napkin or other absorbent structure may take place well before the hydrogel material in the absorbent structure is fully wet.

Water-insoluble hydrogels have a water absorbent capacity which far exceeds, generally by far more than an order of magnitude, the absorbent capacity for water of wood pulp fibrous webs which are typically used in disposable absorbent consumer products. The absorption capacity for an electrolyte containing fluid, like urine, is much less but still up to about an order of magnitude higher than that of fibrous webs. Many workers in the field have therefore attempted to somehow incorporate hydrogel materials into wood pulp fiber webs in order to increase the fluid absorption capacities of such webs. Early attempts involved simple mixing of hydrogel powder into the fibrous web. This approach did not lead to any increase of the bulk absorption capacity of the web. (See, for example, R. E. Ericson, "First International Absorbent Products Conference Proceedings", November, 1980, Section 6 at page 3). Ericson reports that "fluid retention under pressure is increased but bulk capacity remains essentially the same". Several explanations for this phenomenon have been given. Ericson ascribes it to the fact that the fibrous matrix prevents swelling of the hydrogel particles. Others believe that the very poor wicking characteristics of hydrogels are responsible for the disappointing performance. Whatever the cause may be, it is well established that simple mixtures of hydrophilic fibers and hydrogel particles do not have the absorption capacity one would expect on the basis of the respective contributions of the components of such mixtures.

Based upon the assumption that the poor wicking of hydrogels causes their poor performance in disposable absorbent structures, some workers in the field have attempted to improve hydrogel performance by introducing fibers into the hydrogel particles. This may be achieved by wet laying of mixtures of hydrogel particles and hydrophilic fibers. During the wet stage of such a process the hydrogel swells. During the drying step the hydrogel tends to retract. As a result the gel spreads over the fiber surface and creates fiber-fiber bonds, in a manner not dissimilar from the bonding which occurs when binders (e.g. latex) are used. As a result of the wet treatment and the bonding by the hydrogel, the resulting absorbent structure is very stiff. It has been disclosed that the stiffness of such structures may be reduced by subjecting the structure to a high pressure. Even when so treated, the stiffness of such structures is still relatively high, especially when fiber/hydrogel ratios of more than 50:50 are used. Such fiber/hydrogel ratios are, however, very desirable from a cost standpoint: hydrogel is far more expensive than, for example, wood pulp fibers. Moreover, the art-disclosed processes involve the handling of large amounts of water and subsequent drying. This adds significantly to the manufacturing costs of the absorbent structures.

Another approach has been to form laminated structures, whereby a layer of hydrogel material is placed against a layer of a material having good wicking properties. The wicking layer spreads the liquid over a larger surface of the hydrogel layer, so that more of the hydrogel is exposed to the liquid to be absorbed. It has been claimed that such structures provide a higher absorption capacity than e.g. mixtures of hydrogel particles in hydrophilic fibrous webs. The wicking layer provides spreading of the liquid across the surface of the hydrogel layer, but does not ensure penetration into the hydrogel layer. The latter liquid movement is still severely limited by gel blocking. In other words, absorbent structures as they are known in the art fail to fully exploit the absorption potential of hydrogels.

There is therefore a continuing need for absorbent structures which are flexible and which more fully exploit the absorbent capacity of hydrogels than has heretofore been possible. The absorbent structures of the present invention provide superior absorbent capacity and excellent wicking properties, and yet are flexible, resilient, and have good lateral integrity. These structures are uniquely adapted for use in disposable diapers which are extremely thin and comfortable but which have an absorbent capacity which is at least equal to the much bulkier products which are currently marketed. The absorbent structures can be made by a process which does not involve water or another solvent. The process therefore does not involve the handling of solvents, or drying. The simplicity of the process permits the use of standard equipment as is currently being used for the manufacture of absorbent webs; it is possible to implement the manufacture of the absorbent structures of the present invention without any major capital investments, and at low per unit manufacturing costs. It is therefore an object of this invention to provide a flexible absorbent structure which comprises a water-insoluble hydrogel, having improved absorbent properties. It is a further object to provide improved disposable absorbent products, such as diapers, which are substantially thinner and less bulky than conventional disposable absorbent products. It is a further object of this invention to provide a process for making such absorbent structures.

RELEVANT REFERENCES

The gel blocking phenomenon has been well documented, and the resulting poor properties of absorbent structures comprising hydrogels have been discussed: see, for example, E. Carus, "First International Absorbent Products Conference Proceedings", November, 1980, Section V-1; and J. H. Field, "Pulp Parameters Affecting Product Performance", TAPPI, 65(7) 1982, pp. 93–97.

Japanese Patent Specification 56-65630, published June 3, 1981, discloses a process for preparing "tufted lumps" of cellulose fiber holding water-insoluble resins. The lumps are prepared by dispersing the fibers and the resin in methanol, wet-laying the mixture and drying off the solvent. The web is subsequently compressed to a density of more than 0.1 g/cm$^3$, preferably about 0.6 g/cm$^3$. The sheet thus obtained is cut into pieces of less than 0.5 g each. A similar approach is taken by Kopolow, U.S. Pat. No. 4,354,901, issued Oct. 19, 1982. This reference discloses a process whereby a slurry is formed of less than about 0.1% by weight solids in water, the solids being a mixture of cellulose fibers and particulate hydro-colloidal material. A wet web is formed from the slurry which is subsequently dried and densified by at least 10%, preferably at least 50%. It is said that the densifying step results in reduction of the stiffness of the absorbent structure (Gurley Stiffness values of less than 40 g).

SUMMARY OF THE INVENTION

This invention relates to a flexible, substantially unbonded, absorbent structure comprising a mixture of hydrophilic fibers and discrete particles of a water-insoluble hydrogel, in a fiber/hydrogel ratio of from about 30:70 to about 98:2; said absorbent structure having a density of from about 0.15 to about 1 g/cm$^3$.

This invention further relates to a process for making a flexible absorbent structure, comprising the following steps: (a) air-laying a dry mixture of hydrophilic fibers and particles of a water-insoluble hydrogel in a fiber/hydrogel weight ratio of from about 30:70 to about 98:2 into a web; and (b) compressing the web to a density of from about 0.15 to about 1 g/cm$^3$.

BRIEF DESCRIPTION OF THE DRAWING

The drawing schematically illustrates one embodiment of the process for preparing the absorbent structures of the present invention.

DETAILED DESCRIPTION OF THE INVENTION

The basis of this invention is the discovery that mixtures of hydrophilic fibers and particles of water-insoluble hydrogels may be formed into flexible, highly absorbent structures, provided that the weight ratio of fiber/hydrogel is between about 30:70 to about 98:2; and further provided that the structure is densified to a density of from about 0.15 to about 1 g/cm$^3$. The absorbent structures of the present invention are basically webs of hydrophilic fibers, having dispersed therein discrete particles of the water-insoluble hydrogel. The hydrogel particles may be randomly dispersed, or in a pattern of areas with a low fiber/hydrogel ratio, and areas of a high fiber/hydrogel ratio (which includes areas of fiber alone).

By "substantially unbonded" is meant that the number of fiber/fiber bonds, fiber/hydrogel particle bonds and hydrogel particle/hydrogel particle bonds is kept as low as reasonably possible. Bonds which may occur include hydrogen bonds (like paper-making bonds), other types of chemical bonds as may occur between fibers and hydrogel particles, among hydrogel particles, and among certain types of fibers (e.g. thermoplastic fibers) and mechanical bonds. This is important because the high absorbent capacities of the absorbent structures of the present invention are due to a significant extent to their ability to quickly regain volume upon initial wetting. A large number of bonds among the constituents of the structure would seriously impair this ability.

It is virtually impossible to entirely prevent bonds from being formed. However, some modest degree of bonding does not appear to negatively affect the structures' ability to quickly regain volume upon initial wetting. Generally, the degree of bonding is minimized by avoiding exposure of the fibers and hydrogel particles, or the absorbent structures, to water in its liquid form, and by avoiding prolonged exposure to air which has a high relative humidity. These process parameters are discussed in more detail hereinbelow.

By "hydrogel" as used herein is meant an inorganic or organic compound capable of absorbing aqueous fluids and retaining them under moderate pressures. For good results, the hydrogels must be water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarsson et al., Aug. 26, 1975, the disclosures of which are incorporated herein by reference. Particularly preferred polymers for use herein are hydrolyzed acrylonitrile grafted starch, acrylic acid grafted starch, polyacrylates, and isobutylene maleic anhydride copolymers, or mixtures thereof.

Processes for preparing hydrogels are disclosed in U.S. Pat. No. 4,076,663, issued Feb. 28, 1978 to Fusayoshi Masuda e al.; in U.S. Pat. No. 4,286,082, issued Aug. 25, 1981 to Tsuno Tsubakimoto et al.; and further in U.S. Pat. Nos. 3,734,876, 3,661,815, 3,670,731, 3,664,343, 3,783,871, and Belgian Pat. No. 785,858; the disclosures of all of which are incorporated herein by reference.

As used herein "Particles" include particles of any shape, e.g. spherical or semi-spherical, cubic, rod-like, polyhedral, etc.; but also shapes having a large greatest dimension/smallest dimension ratio, like needles, flakes and fibers, are contemplated for use herein. By "particle size" as used herein is meant the weight average of the smallest dimension of the individual particles. Conglomerates of hydrogel particles may also be used, provided the weight average size of such conglomerates is within the limits set forth hereinbelow.

Although the absorbent structures of the present invention are expected to perform well with hydrogel particles having a particle size varying over a wide range, other considerations may preclude the use of very small or very large particles. For reasons of industrial hygiene, (weight) average particle sizes smaller than about 30 microns are less desirable. Particles having a smallest dimension larger than about 4 mm may cause a feeling of grittiness in the absorbent structure, which is undesirable from a consumer standpoint. Preferred for use herein are particles having an (weight) average particle size of from about 50 microns to about 1 mm.

The type of hydrophilic fibers is not critical for use in the present invention. Any type of hydrophilic fiber which is suitable for use in conventional absorbent products is also suitable for use in the absorbent structure of the present invention. Specific examples include cellulose fibers, rayon, polyester fibers. Other examples of suitable hydrophilic fibers are hydrophilized hydrophobic fibers, like surfactant-treated or silica-treated thermoplastic fibers. Also, fibers which do not provide webs of sufficient absorbent capacity to be useful in conventional absorbent structures, but which do provide good wicking properties, are suitable for use in the absorbent structures of the present invention. This is so because, for the purposes of the present invention, wicking properties of the fibers are far more important than their absorbent capacity. For reasons of availability and cost, cellulose fibers, in particular wood pulp fibers, are preferred.

The relative amount of hydrophilic fibers and hydrogel particles are most conveniently expressed in a weight ratio fiber/hydrogel. These ratios may range from about 30:70 to about 98:2. Low fiber/hydrogel ratios, i.e. from about 30:70 to about 50:50, are practicable only when the hydrogel used possesses a low swelling capacity i.e., hydrogels having an absorbent capacity for urine and other body fluids of less than about 15 times their own weight ($15\times$). (Absorbent capacity data are generally available from the manufacturer of the hydrogel; or may conveniently be determined by means of the absorption/desorption test described hereinbelow). Hydrogels which have a very high absorption capacity (i.e. $25\times$, and which consequently exhibit a high degree of swelling after wetting) tend to gel block when used in absorbent structures at low fiber/hydrogel ratios, which causes undesirable, slow, diffusion type absorption kinetics. Very high fiber/hydrogel ratios, e.g. above 95:5 on the other hand, provide meaningful performance benefits only if the hydrogel used has a high absorbent capacity (e.g., $25\times$ for urine and other body fluids). For most commercially available hydrogels the optimum fiber/hydrogel ratio is in the range of from about 50:50 to about 95:5.

Based on a cost/performance analysis, fiber/hydrogel ratios of from about 75:25 to about 90:10 are preferred. This preference is, of course, based on the relative costs of hydrophilic fibers (e.g. wood pulp fibers) and hydrogel. If, for example, wood pulp prices would go up and/or hydrogel prices would come down, lower fiber/hydrogel ratios would be more cost effective.

The density of the absorbent structure is of critical importance. When hydrogel particles are dispersed into an absorbent web of hydrophilic fibers having a density of about 0.1 g/cm$^3$, the admixture of the hydrogel results in only a small increase in the amount of fluid which is absorbed within a practicably reasonable time (e.g. 10 minutes) because the fluid uptake of such webs is slow. When the absorbent structure is densified to a density of at least about 0.15 g/cm$^3$, a marked increase in absorbent capacity is observed. Moreover, the fluid uptake becomes much faster upon densification. The capacity increase is surprising because densifying the web will result in reducing the void volume of the dry structure. It is believed that densifying the web results in better wicking of fluid into the web, so that more hydrogel particles participate in the absorption process, which results in a higher actual absorbent capacity. It is further believed that a densified web may be more effective in keeping the hydrogel particles isolated from each other. Densifying the web further, from about 0.15 g/cm$^3$ to about 1 g/cm$^3$, results in a reduction in the bulk of the structure (which is desirable from a consumer standpoint, for aesthetics reasons), without loss of absorbent capacity. However, above a density of about 0.6 g/cm$^3$, further densification hardly reduces the bulk further, because of the inverse relationship between bulk and density. The densities of the absorbent structures of the present invention are therefore preferably in the range of from about 0.15 to about 0.6 g/cm$^3$, and more preferably within the range of from about 0.25 to about 0.4 g/cm$^3$.

The continuous flexible absorbent structures of the present invention can be made by a process comprising the steps of (a) air-laying a dry mixture of hydrophilic fibers and particles of a water-insoluble hydrogel in a weight ratio of from about 30:70 to about 98:2; and (b) compressing the web to a density of from about 0.15 to about 1 g/cm$^3$. Step (a) may be accomplished by metering an air flow containing hydrophilic fibers and an air flow containing hydrogel particles onto a wire screen. The fibers and the particles become mixed by turbulence of the two air flows as they meet. Alternatively, the fibers and the hydrogel may be mixed in a separate mixing chamber prior to air-laying.

For the purpose of the present invention it is essential that dry hydrogel particles are used. Also, neither the fibers, the particles nor the mixture of fibers and particles should be exposed to water in its liquid form, or another solvent, at any time during this process or subsequent thereto. When wet hydrogel particles are used, the fibers tend to become entangled and/or bonded with the particles which results in undesirable stiffness of the absorbent structure. Especially when cellulose fibers, e.g. wood pulp fibers, are used as the hydrophilic fibers in the absorbent structures of the present invention, the softness of these structures can be improved by adding small quantities of chemical debonding agents (cationic, nonionic or anionic surfactants) to the fibers. Examples of suitable debonding agents are disclosed in U.S. Pat. No. 3,821,068, issued June 28, 1974 to Shaw, the disclosures of which are incorporated herein by reference. Particularly suitable debonding agents are quaternary ammonium compounds of the type disclosed in U.S. Pat. No. 3,554,862, issued Jan. 12, 1971 to Hervey et al., incorporated herein by reference. Preferred quaternary ammonium compounds are those having the general formula

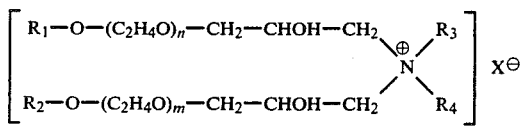

wherein $R_1$ and $R_2$ are hydrocarbyl groups containing from about 8 to about 22 carbon atoms, $R_3$ and $R_4$ are alkyl having from 1 to 6 carbon atoms; n and m are integers from 2 to about 10, and X is halogen. Examples of such compounds are disclosed in U.S. Pat. No. 4,144,122, issued Mar. 13, 1979 to Emanuelsson et al., incorporated herein by reference.

Typically, the amount of chemical debonding agent in the absorbent structures is from about 0.01% to about 0.5% by weight of the hydrophilic fibers.

As used herein, "dry" does not mean "absolutely water-free". For example, under normal storage and handling conditions, hydrogel particles take up some moisture. The hydrophilic fibers also take up some moisture during storage. Furthermore, it may be desirable to use humidified air for air transport of the fibers and the hydrogel particles, to avoid dusting. Under such process conditions, the hydrogel particles and the fibers will take up even more moisture, but this does not negatively affect the practice of the present invention. However, contact times of the hydrogel with conveying air are short, and the limited water-uptake by the hydrogel during air-conveying with humidified air will not result in substantial bonding of the structure. The important criterion is that the hydrogel particles should not be allowed to swell appreciably, and should not develop a surface stickiness to a point that it results in entanglement and/or bonding of the fibers. Generally, this can be achieved by exposing the hydrophilic fibers and the hydrogel particles only to water vapor, and not to water in its liquid form. Even mere exposure of the hydrogel to humidified air may result in substantial bonding of the structure during subsequent processing, especially during calendering, if such exposure is prolonged. For example, in U.S. Pat. No. 4,252,761, issued Feb. 24, 1981 to Schoggen et al., the entire thrust is to expose specific hydrogel imaterials to levels of water which result in bonded structures which are unacceptable for the purpose of the present invention due to unacceptable initial absorption kinetics. In order to ensure that the structure remains substantially unbonded the moisture content of the absorbent structure must be less than about 10% by weight of the dry absorbent structure.

The absorbent structures may conveniently be made by using conventional equipment designed for air laying of hydrophilic fibrous webs. In such equipment, webs are typically formed by taking up hydrophilic fibers in an air flow and depositing the fibers on a wire mesh screen. By metering the desired quantities of hydrogel particles into the air flow at a point just upstream of the wire mesh screen, the desired mixture of hydrophilic fibers and hydrogel particles can be made. The web formed on the screen is then passed through calender rolls which are set to a nip pressure resulting in the desired density of the absorbent structure. It will be clear that this embodiment of the process requires only minor modifications of conventional equipment for the manufacture of absorbent structures, i.e. installing a metering device for the addition of the hydrogel particles. In certain instances it may be necessary to replace the standard wire mesh screen on the equipment with one of a finer mesh size. This need will arise when relatively small hydrogel particles are used, and/or when the mesh size of the standard screen is relatively coarse.

The process of preparing the absorbent structures of the present invention is illustrated by the drawing. In this process sheets of dry lap 101 are fed to a hammer mill 102 wherein the dry lap is disintegrated into cellulose fibers. Such fibers are blown from the hammer mill using air entering through conduit 103. Particles of hydrogel 104 are fed to the system from a hydrogel feed hopper 105 via conduit 106. The mixture 107 of cellulose fibers and hydrogel particles is removed from the hammer mill via conduit 108 and propelled through conduit 109 by an airstream. An intimate admixture of the fibers and hydrogel particles is formed in the conduit 109.

The mixture 107 of cellulose fibers and hydrogel particles is deposited on the screen surface 110 of a forming drum 111, the inside of which is maintained under vacuum. The mixture of cellulose fibers and hydrogel particles intermittently deposited on the screen forms discrete fiber webs 112 on the surface of the forming drum. These webs 112 are removed from the forming drum and deposited onto a transfer screen 113. The webs 112 on the transfer screen then pass between upper and lower calender rolls 114 and 115 which serve to compress the webs 112 to the desired density, thereby forming the absorbent structures of the present invention.

Because of their particular properties, the absorbent structures of this invention are extremely suitable for use in disposable absorbent products. By "absorbent product" herein is meant a consumer product which is capable of absorbing significant quantities of water and other fluids, like body fluids. Examples of absorbent products include disposable diapers, sanitary napkins, incontinence pads, paper towels, facial tissues, and the like. As compared to conventional hydrophilic fibrous webs, the absorbent structures of this invention have a high absorbent capacity, a high density, and a flexibility which is at least equal to that of conventional fibrous webs. For these reasons, these absorbent structures are particularly suitable for use in products like diapers, incontinent pads, and sanitary napkins. The high absorbent capacity and the high density make it possible to design absorbent products which are thin and yet have more than sufficient absorbent capacity to avoid the embarrassment of failure. Flexibility of the structure ensures comfort for the wearer and a good fit of the absorbent product. The high density/low volume of the products will also result in important packaging and transport cost savings for the manufacturer.

Disposable diapers comprising the absorbent structures of the present invention may be made by using conventional diaper making techniques, but replacing the wood pulp fiber web ("air-felt") core which is typically used in conventional diapers with an absorbent structure of the present invention. Thus, a disposable diaper may be comprised of (from top to bottom) a top sheet (a non-woven, hydrophobic tissue, e.g. needle punched polyester), the absorbent structure, and a waterproof, pliable back sheet (e.g. hard polyethylene, having an embossed caliper of approximately 2.3 mils.). Optionally, the absorbent structure may be wrapped in envelope tissue (wet strength tissue paper). Disposable diapers of this type are disclosed in more detail in U.S.

Pat. No. 3,952,745, issued Apr. 27, 1976 to Duncan; and in U.S. Pat. No. 3,860,003, issued Jan. 14, 1975 to Buell, the disclosures of which are incorporated herein by reference.

Since the absorbent structures of the present invention have a higher absorbent capacity than conventional wood pulp fiber webs, the wood pulp web may be replaced with an absorbent structure of the present invention of less than equal weight. The reduced weight and the higher density combined account for a reduction in bulk by a factor 3 to 12 or more (depending on the type of hydrogel, the fiber/hydrogel ratio, and the density used).

The amount of absorbent structure used in disposable diapers is conveniently expressed as the basis weight (in $g/cm^2$) of the structure. Typically, basis weights of the absorbent structures of the present invention as used in disposable diapers range from about 0.01 $g/cm^2$ to about 0.05 $g/cm^2$. One way in which this invention may be used is in manufacturing diapers having both increased absorption capacity and reduced bulk as compared to conventional diapers. This can be obtained by using absorbent structures having a basis weight of from about 0.018 to about 0.03 $g/cm^2$. Preferred are basis weights of from about 0.019 to about 0.021 $g/cm^2$. A different approach is to aim at an absorbent capacity substantially equivalent to that of conventional diapers, while fully exploiting the potential of bulk reduction offered by this invention. This is generally achieved by using basis weights of from about 0.01 to about 0.017 $g/cm^2$. Preferred are basis weights in the range from about 0.014 to about 0.017. The absorbent structures used in disposable diapers preferably have a thickness of from about 0.3 mm to about 2 mm, more preferably from about 0.5 mm to about 1 mm.

Conventional disposable diapers are usually comprised of (from top to bottom) a top sheet (a non-woven, hydrophobic tissue, e.g., needle punched polyester), a wood pulp fiber absorbent core, and a waterproof, pliable back sheet (e.g., hard polyethylene having an embossed caliper of approximately 2.3 mils.). The absorbent capacity of such diapers is substantially increased when an absorbent structure of the present invention is placed between the wood pulp fiber core and the back sheet. When used in this manner the absorbent structures preferably have a thickness of from about 0.1 mm to about 1 mm. The absorbent structure used as an insert can have the same size and shape as the wood pulp fiber core, or be different. In a specific embodiment the wood pulp fiber core is hourglass shaped (i.e., the width in the center of the core is substantially less than the width at the ends), and the absorbent structure is rectangular, having a length approximately the same as the length of the wood pulp fiber core, and a width of from about 1 cm to about 5 cm less than the width of the wood pulp fiber core at the narrowest point of the hourglass.

Because the absorbent structures of the present invention are highly absorbent, and yet thin and flexible, they are extremely suitable for use in sanitary napkins. As is the case with disposable diapers, sanitary napkins utilizing the present absorbent structures may be derived from conventional sanitary napkins by simply replacing the absorbent core thereof (typically a web of wood pulp fibers) with an absorbent structure of the present invention. Such replacement may be on a weight-by-weight basis, which results in a reduction in volume and a gain in capacity; or the replacement may be on a less than equal weight basis, thereby sacrificing part of the gain in absorbent capacity in favor of an even greater reduction in bulk. The absorbent structures used in sanitary napkins preferably have a thickness of from about 0.1 mm to about 2 mm, more preferably from about 0.3 mm to about 1 mm.

An example of a sanitary napkin comprises a pad of the absorbent structure of the present invention; a hydrophobic topsheet; and a fluid impervious bottom sheet. The topsheet and the backsheet are placed at opposite sides of the absorbent structure. Optionally, the absorbent structure is wrapped in envelope tissue. Suitable materials for top sheets, bottom sheet and envelope tissue are well known in the art. A more detailed description of sanitary napkins and suitable materials for use therein is found in U.S. Pat. No. 3,871,378, issued Mar. 18, 1975 to Duncan et al., the disclosures of which are incorporated herein by reference.

PERFORMANCE TESTING

A. Partitioning Test

Samples of absorbent structures were subjected to a partitioning test, more fully described hereinbelow. This test has been designed to measure the absorption performance of absorbent structures in competition with conventional cellulose fibrous webs, both under conditions of low liquid load and high liquid loads. The absorption fluid was "synthetic urine" (a solution of 1% NaCl, in distilled water; the surface tension of the solution was adjusted to 45 dynes/cm with about 0.0025% of an octylphenoxy polyethoxy ethanol surfactant (Triton X-100, from Rohm and Haas Co.). This test has been found to be predictive of the absorption capacity under typical usage conditions of absorbent structures when used as absorbent cores in diapers.

Absorbent structures were made by metering predetermined amounts of hydrogel particles into a flow of air containing southern soft wood slash pine fibers; the mixture was air laid on a wire mesh screen and the resulting web was densified between calender rolls to the required density. The structures had a basis weight of 0.04 $g/cm^2$. On the same equipment, webs of southern soft wood slash pine fibers were made, also having a basis weight of 0.04 $g/cm^2$ and calendered to a density of 0.1 $g/cm^3$. No hydrogel particles were added to the latter webs. The latter web served as the reference in all tests. Round samples of 6 cm diameter were punched out of the sheets of absorbent material for partitioning testing.

The partitioning tests were carried out as follows. A piece of polyethylene sheet (the kind of material generally used as a backsheet in disposable diapers) was placed on a flat, nonabsorbent surface. A round sample (6 cm diameter) of the absorbent structure to be tested was placed on top of this backsheet. On top of that was placed a piece of paper tissue of the type generally used as envelope tissue in disposable diapers. On top of the envelope tissue was placed a sample of the reference material (southern soft wood slash pine fibrous web, 0.1 $g/cm^3$ density). The top sample was wetted with a predetermined amount (about 1 g) of synthetic urine, covered with another piece of backsheet, upon which a weight of 4.4 pounds (about 2 kg) was placed. This weight exerts a confining pressure of 1 psi (about $70 \times 10^3 N/m^2$). After five minutes equilibration time, the weight was removed and the two samples of absorbent material were weighed separately. The "loading", defined as the amount of synthetic urine (in grams)

absorbed per gram of absorbent material was calculated for each sample. The sample was then dosed with an additional dose of synthetic urine, placed back under the confining weight, equilibrated, and weighed. This was repeated several times (typically on the order of 8-10 times) so that the relative absorption performance of the test material over a wide range of total loadings was obtained. The loading of the bottom test layer was then plotted as a function of the loading in the reference top layer.

Of particular interest are the loadings of the test layer at the points where the loading of the reference is 2.0 g/g and 4.5 g/g respectively. The loading of the test layer at the reference loading of 4.5 g/g has been found to be predictive of the loading at failure in normal use when the test material is used as a core in a disposable diaper. The loading of the test layer at a loading of the reference layer of 2.0 g/g is representative of the loading of the diaper under typical usage conditions. All experimental results reported herein are average results of duplicate or triplicate experiments.

B. Absorption/Desorption Test

The absorption properties of absorbent structures were determined by their "synthetic urine" absorption and desorption behavior. The basis procedure and the design of the apparatus are described by Burgeni and Kapur, "Capillary Sorption Equilibria in Fiber Masses", *Textile Research Journal*, 37 (1967) 362, which publication is incorporated herein by reference. The test is particularly useful for determining absorption kinetics.

The absorption apparatus consisted of a horizontal capillary tube, approximately 120 cm long, connected by a valve to a fluid reservoir. The end of the tube was connected by tygon tubing to a glass funnel containing an ASTM 4-8 micron frit on which the absorbent web sample was placed. The glass frit funnel was mounted on a vertical pole. The height of the frit above the capillary tube determined the hydrostatic suction being exerted on the sample. In a typical absorption/desorption experiment the volume of absorbed synthetic urine was determined as a function of hydrostatic suction, starting at 100 cm (corresponding with a hydrostatic pressure of −100 cm).

A simplified test was developed to determine the useful capacity of an absorbent web. In this test, the absorbed volume at −25 cm hydrostatic pressure was measured ("25 cm, absorption"). Next, the frit containing the sample was lowered to zero hydrostatic pressure and the equilibrium value of sorbed volume measured ("0 cm, void volume"). Then the frit was raised again to the 25 cm mark and the absorbed volume at −25 cm in the desorption mode was determined ("25 cm, desorption").

C. Gurley Stiffness Test

The stiffness of absorbent structures was determined using a Gurley Stiffness Tester (manufactured by W. and L. E. Gurley of Troy, New York). The use of this tester is disclosed in U.S. Pat. No. 4,354,901, issued Oct. 19, 1982 to Kopolow, which disclosure is incorporated herein by reference. In essence, this instrument measures the externally applied force required to produce a given deflection of a strip of material of specific dimensions, fixed at one end and having a load applied to the other end. The results were obtained as "Gurley Stiffness" values in units of grams. Each strip of absorbent material was 3.5 inches by one inch (about 8.9 cm×2.5 cm).

The absorbent structures of the present invention have a Gurley Stiffness value of less than 2 g, preferably less than about 1 g, when measured on a strip having a basis weight of 0.03 g/cm$^2$.

EXAMPLE I

In order to test the effect of fiber:hydrogel ratios on the partitioning performance of absorbent structures, the following absorbent structures were prepared.

Southern soft wood slash pine fibers were dry mixed with an acrylic acid grafted starch hydrogel having a weight average particle size of about 250 microns ("Sanwet IM 1000", from Sanyo Co., Ltd., Japan) in fiber:hydrogel ratios of 100:0 (no hydrogel), 95:5, 90:10, 85:15, and 80:20. Webs having dimensions of 41×30 cm, and having a basis weight of 390 g/m$^2$, were prepared in a batch type air laying equipment. The webs were compressed to a dry density of 0.3 g/cm$^3$, using a flat hydraulic press, corresponding to a thickness of 1.3 mm.

Samples of these webs were subjected to the above-described partitioning test. The following results were obtained:

TABLE I

Partitioning performance of absorbent structures as a function of fiber:hydrogel ratio.

| Fiber:Hydrogel Ratio | Loading (g/g) at Reference = 2.0 g/g | Loading (g/g) at Reference = 4.5 g/g |
|---|---|---|
| 100:0 | 2.0 | 3.6 |
| 95:5 | 2.4 | 4.5 |
| 90:10 | 3.4 | 5.9 |
| 85:15 | 3.7 | 6.5 |
| 80:20 | 4.0 | 7.2 |

TABLE II

Absorption/desorption data[1] as a function of fiber:hydrogel ratio

| Fiber:Hydrogel Ratio | 25 cm Absorption | 0 cm Void | 25 cm Desorption |
|---|---|---|---|
| 100:0 | 2.5 | 3.0 | 2.9 |
| 95:5 | 2.9 | 3.8 | 3.5 |
| 90:10 | 3.8 | 4.9 | 4.5 |
| 85:15 | 4.3 | 5.9 | 5.3 |
| 80:20 | 4.8 | 6.2 | 5.8 |

[1]in ml/g, after 10 min. equilibration time

The data demonstrate the dramatic increase in absorption capacities over a wide range of conditions which is obtained by the absorbent structures of the present invention, as compared to all-fiber structures of the same density.

EXAMPLE II

For comparison, absorbent structures were prepared, using the wet-laying process described in U.S. Pat. No. 4,354,901 (issued Oct. 19, 1982 to Kopolow) as follows:

A mixture of southern slash pine wood pulp fibers and an acrylic acid grafted starch hydrogel material (Sanwet IM 1000, from Sanyo Co., Ltd., Japan) (fiber:hydrogel ratio=80:20) was slurried in water at a consistency of 0.7%. A web was formed by straining the slurry on a wire mesh screen. The amount of slurry was such as to result in a basis weight of 0.034 g/cm$^2$. The web was dried in an oven at 100° C. The density of the dried web was about 0.2 g/cm$^3$. The web was then compressed in a hydraulic press to a density of 0.38 g/cm$^3$. The resulting structure was stiff and board-like.

The absorption performance of this sample was determined with the above-described partitioning test. The results are compared with those obtained with an air-laid structure prepared according to the process of the present invention. (Table III)

TABLE III

Partitioning performance of absorbent structures as affected by the process of making.

| Fiber:Hydrogel Ratio[1] | Process | Loading (g/g) at Ref. = 2.0 g/g | Loading (g/g) at Ref. = 4.5 g/g |
|---|---|---|---|
| 80:20 | Air-laying[2] | 4.0 | 7.2 |
| 80:20 | Wet-laying[3] | 3.4 | 4.5 |

[1]density of both structures was 0.3 g/cm²
[2]according to the process of the present invention
[3]process as described in U.S. Pat. No. 4,354,901

The data demonstrate that the process of the present invention results in absorbent structures having absorbent properties which are far superior to those made by a wet-laying process.

EXAMPLE III

The following structures were prepared using the above-described air-laying technique: an all-fiber (southern slash pine) web, density 0.1 g/cm³ (sample A); an all-fiber (southern slash pine) web, density 0.3 g/cm³ (sample B); a fiber (southern slash pine)/hydrogel structure (fiber:hydrogel ratio=80:20), density 0.3 g/cm³ (sample C). The hydrogel was the same as used in Examples I and II. All structures were soft and flexible.

The partitioning performance of these samples was determined using the above described partitioning test, except that equilibration times were one minute.

TABLE IV

Partitioning Performance of Various Absorbent Structures

| Sample # | Loading (g/g) at Reference = 2.0 g/g | Loading (g/g) at Reference = 4.5 g/g |
|---|---|---|
| A | 1.1 | 4.4 |
| B | 2.1 | 3.9 |
| C* | 3.4 | 7.1 |

*structure according to the present invention

The partitioning data illustrate that densifying an all-fiber structure (A-B) results in a higher partitioning capacity at low loading (due to better wicking), but a lower capacity at high loading (due to reduce void volume). An 80:20 fiber:hydrogel mixture at high density (0.3 g/cm³, sample C) possesses vastly superior partitioning properties, both at low and at high loadings.

EXAMPLE IV

Absorbent structures containing different types of hydrogel were made by in-line metering of dry hydrogel particles into a flow of southern softwood slash pine fibers. All hydrogel samples had a weight average particle size in the range of from 100 microns to 1 mm. The mixture were formed into sheets, basis weight of about 0.035 g/cm², on a wire screen. The sheets were compressed to a dry density of 0.3 g/cm³.

The partitioning performance of each sheet was tested with the above-described partitioning test. The results are collected in Table V.

TABLE V

| Type of Hydrogel | Fiber:Hydrogel Ratio | Loading at Ref. = 2.0 g/g | Loading at Ref. = 4.5 g/g |
|---|---|---|---|
| None (control) | 100:0 | 2.05 | 3.60 |
| Starch, acrylonitrile[1] | 81.2:18.8 | 3.45 | 5.35 |
| Starch, acrylonitrile[2] | 84.6:15.4 | 2.30 | 5.40 |
| Polyacrylate[3] | 75.0:25.0 | 5.75 | 8.65 |
| Polyacrylate[3] | 80.8:19.2 | 5.10 | 8.10 |
| Starch, acrylonitrile[4] | 82.7:17.3 | 4.25 | 6.10 |
| Starch, acrylonitrile[4] | 78.7:21.3 | 4.25 | 6.10 |
| Starch, acrylonitrile[5] | 82.6:17.4 | 4.00 | 5.40 |
| Cellulose, carboxyl[6] | 86.0:14.0 | 2.95 | 5.14 |
| Cellulose, carboxyl[6] | 77.9:22.1 | 3.20 | 5.40 |
| Starch, carboxyl[7] | 82.1:17.9 | 2.20 | 4.40 |
| Starch, acrylic acid[8] | 80.1:19.9 | 3.55 | 7.00 |
| Starch, acrylic acid[8] | 77.7:22.3 | 4.40 | 7.40 |
| Isobutylene/maleic anhydride copolymer[9] | 77.6:22.4 | 4.25 | 7.75 |
| Isobutylene/maleic anhydride copolymer[9] | 80.0:20.0 | 4.25 | 7.45 |

[1]A-100, from Grain Processing
[2]A-200, from Grain Processing
[3]J-550, from Grain Processing
[4]SGP 147, from Henkel, U.S.A.
[5]SGP 502SB, from Henkel, U.S.A.
[6]Akucell 3019, from Enka, Germany
[7]Foxorb 15, from Avebe, France
[8]Sanwet IM 1000, from Sanyo, Japan
[9]KI Gel 201, from Kuraray, Japan As the results indicate, the presence of hydrogel particles in a densified hydrophilic fibrous web results in a significant increase in partitioning capacity, both at low load and at high load conditions.

Similar structures are prepared, wherein the southern softwood Kraft pulp fibers are replaced with hardwood Kraft pulp fibers; chemo-thermo mechanical softwood fibers; eucalyptus Kraft pulp fibers; cotton fibers; and polyester fibers. Substantially similar results are obtained.

EXAMPLE V

Absorbent structures were made by the batch-type process described in Example I. Southern softwood Kraft pulp fibers were used in admixture with an acrylic acid grafted starch hydrogel ("Sanwet IM 1000", from Sanyo Co., Ltd., Japan). This type of hydrogel has a saturation capacity for "synthetic urine" of about 25×.

Samples of various fiber/hydrogel ratios were prepared. The kinetics of synthetic urine absorption of these samples was studied in the absorption/desorption apparatus described hereinabove. The synthetic urine used in this test was a solution of 1% NaCl, 0.06% $MgCl_2.6H_2O$ and 0.03% $CaCl_2.2H_2O$ in distilled water; the surface tension of the solution was adjusted to 45 dynes/cm with about 0.0025% of an octyl phenoxy polyethoxy ethanol surfactant (Triton X-100, from Rohm and Haas Co.). All absorbent structures had a density of 0.3 g/cm³ and a basis weight of about 0.04 g/cm². All absorption kinetics were measured under a confining pressure of 1 psi (about $70 \times 10^3 N/m^2$), which closely approaches real-life conditions for use in diapers.

TABLE VI

Absorption kinetics; hydrostatic pressure −25 cm; absorption mode

| Time (min.) | Absorption (ml/g) Fiber/hydrogel ratio (g/g) | | | | |
|---|---|---|---|---|---|
| | 100:0 | 88:12 | 73:27 | 48:52 | 34:66 |
| 5 | 2.8 | 3.8 | 4.9 | 3.8 | 2.7 |

TABLE VI-continued

| | Absorption kinetics; hydrostatic pressure −25 cm; absorption mode | | | | |
|---|---|---|---|---|---|
| Time (min.) | Absorption (ml/g) Fiber/hydrogel ratio (g/g) | | | | |
| 10 | 2.8 | 4.2 | 5.8 | 4.6 | 3.2 |
| 30 | 2.8 | 4.4 | 6.4 | 5.9 | 4.5 |
| 60 | — | 4.5 | 6.6 | 7.0 | 5.7 |
| 360 | — | 4.6 | 7.0 | 9.8 | 9.1 |
| 720 | — | — | 7.2 | 11.0 | 10.6 |

The data indicate that the equilibrium absorption capacity increases with increasing amounts of hydrogel. The data also demonstrate, however, that the rate at which the equilibrium absorption capacity is approached becomes progressively slower with increasing amounts of hydrogel.

The optimum fiber/hydrogel ratio for this specific fiber-hydrogel system under these testing conditions appears to be around 75:25.

A similar picture is obtained with 0 cm-void volume absorption kinetics, but there are interesting differences (Table VII). Since under these test conditions the wicking properties are less important, the relative performance of the absorbent structures is to a larger extent determined by the equilibrium absorption capacities of these structures. Still, a structure which has very poor absorption kinetics (i.e., fiber/hydrogel ratio of 40:60) is deficient at times 60 min. as compared to 61:39 and 53:47 fiber/hydrogel samples even under 0 cm hydrostatic pressure conditions.

TABLE VII

| | Absorption kinetics; hydrostatic pressure 0 cm | | | | | |
|---|---|---|---|---|---|---|
| Time (min.) | Absorption (ml/g) Fiber/Hydrogel Ratio (g/g) | | | | | |
| | 100:0 | 88:12 | 78:22 | 61:39 | 53:47 | 40:60 |
| 5 | 4.2 | 5.9 | 6.8 | 7.7 | 7.5 | 6.6 |
| 10 | 4.2 | 6.3 | 7.5 | 8.8 | 8.6 | 7.6 |
| 30 | 4.2 | 6.5 | 8.3 | 10.2 | 10.0 | 9.3 |
| 60 | — | 6.6 | 8.5 | 10.7 | 10.7 | 10.5 |
| 360 | — | 6.8 | 8.9 | 11.7 | 12.1 | 13.8 |

It is expected that, when similar samples are prepared with southern softwood Kraft pulp fibers and a hydrogel which has a saturation capacity for "synthetic urine" of about 10×, the absorption capacities will be lower for each fiber/hydrogel ratio than those given in Table VII. However, for these mixtures, a fiber/hydrogel ratio of 40:60 is expected to perform better than a fiber/hydrogel ratio of 50:50 at 5 and 10 min. equilibration times, contrary to the picture obtained with the above hydrogel having a saturation capacity of 25×.

EXAMPLE VI

Absorbent structures were made according to the process of the present invention, as described in Example I. The fiber/hydrogel weight ratio was 80:20. The Gurley Stiffness values of these structures were determined. For comparison, the Gurley Stiffness values of structures made according to the wet-laying process described in U.S. Pat. No. 4,354,901 (see Example II) were determined before and after densification. (Table VIII)

TABLE VIII

| Sample | Density (g/cm$^3$) | Basis Weight (g/cm$^2$) | Gurley Stiffness (g) |
|---|---|---|---|
| Wet-laid | 0.1 | 0.037 | 24.4 |

TABLE VIII-continued

| Sample | Density (g/cm$^3$) | Basis Weight (g/cm$^2$) | Gurley Stiffness (g) |
|---|---|---|---|
| Wet-laid | 0.1 | 0.037 | 27.2 |
| Wet-laid | 0.3 | 0.033 | 5.4 |
| Wet-laid | 0.3 | 0.033 | 3.8 |
| Air-laid | 0.3 | 0.032 | 0.24 |
| Air-laid | 0.3 | 0.032 | 0.25 |
| Air-laid | 0.3 | 0.035 | 0.64 |
| Air-laid | 0.3 | 0.035 | 0.56 |

The data confirm that the Gurley Stiffness value of a wet-laid structure, which is initially very high, may be reduced by compressing the structure to a higher density, as is disclosed in U.S. Pat. No. 4,354,901. The data further show that the Gurley Stiffness values of the air-laid structures of the present invention are an order of magnitude lower than those of compressed wet-laid structures, and up to 2 orders of magnitude lower than those of uncompressed wet-laid structures.

EXAMPLE VII

A disposable diaper utilizing an absorbent structure according to this invention was prepared as follows:

An absorbent structure prepared as in Example I was calendered to a caliper of about 0.1 cm and a density of about 0.3 g/cm$^3$ as measured under a confining pressure of 0.1 PSI (about 7×10$^3$N/m$^2$). The web was cut into pads of 12 in. × 16 in. (about 30×40 cm). The pads were enveloped in wet strength tissue paper having a basis weight of about 12 pounds per 3,000 square feet (about 20 g/m$^2$), a dry tensile strength of about 700 g/inch in the machine direction and about 300 g/inch in the cross machine direction.

The enveloped pad was glued onto a 13 in. × 17 in. (about 33 cm×43 cm) backsheet of embossed polyethylene film having a melt index of about 3 and a density of about 0.92 g/cm$^3$. The ends of the backsheet were folded over the enveloped pad and attached with glue. Finally, the absorbent pad was covered with a topsheet of a hydrophobic but water and urine pervious material. (Webline No. F 6211 from the Kendall Co. of Walpole, Mass., comprised of a non-woven rayon bonded with an acrylic latex).

The diapers had superior water and synthetic urine absorption, wicking and containment characteristics.

EXAMPLE VIII

Sanitary napkins employing an absorbent structure pursuant to this invention are prepared as follows:

An absorbent structure, prepared as in Example I, is calendered to a caliper of about 0.07 cm and a density of about 0.4 g/cm$^3$ as measured under a confining pressure of 0.1 PSI (about 7×10$^3$N/m$^2$). The web is cut into a pad of 8 in.×2 in. (about 20 cm×5 cm) with tapered ends. On top of this pad is placed a second pad (rectangular) of 5 in.×2 in. (about 13 cm×5 cm). The combined pad structure is placed against a waterproof backing sheet (8 in.×2 in., tapered) of embossed hard polyethylene having an embossed caliper of 2.3 mils. The structure is covered with a top sheet of non-woven, 3 denier needle punched polyester fabric having a density of about 0.03 g/cm$^3$ and a caliper of about 2.3 mm. The thus covered structure is placed on a 9 in.×3 in. (about 23 cm×7.5 cm) bottom sheet of hydrophobic, spinbonded non-woven polyester having a measured weight of about 15 g/m$^2$. The bottom sheet is prefolded upwardly by means of heat and pressure which bonds the superposed sheets together. The resulting absorbent structure is useful as a sanitary napkin and has superior properties of absorption and containment of menses exudate.

EXAMPLE IX

Diapers containing the absorbent structures of the present invention were made as described in Example VII. Control diapers of the same design were made, using wood pulp fiber webs of 0.1 g/cm$^3$ density instead of the absorbent structures of 0.3 g/cm$^3$ density.

The diapers were worn by normal infants. The infants were allowed to play in a nursery school setting during the test. The diapers were left on the infants until leakage occurred. In order to speed up the test, the diapers were pre-loaded with a predetermined amount of synthetic urine.

After leakage occurred, the diapers were taken off and weighed to determine the amount of absorbed fluid. The loading X, defined as the amount of fluid (in grams) absorbed at the point that failure occurred per gram of absorbent material, was calculated. The results are presented in Table IX.

The absorbent core of conventional diapers (samples A, G and I) contain about 5 times their own weight of fluid at the point of leakage. The absorbent structures of the present invention contain from 8.0 to 12.7 times their own weight of fluid at the point where leakage occurs. The data further show that the present invention makes it possible to reduce the volume of a diaper core by a factor 7 (as compared to conventional airfelt diaper cores) while maintaining the absorption capacity of the diaper (compare sample J with samples A, G and I).

EXAMPLE XI

Diapers were prepared as described in U.S. Pat. No. 3,860,003, Buell, issued Jan. 14, 1975, incorporated herein by reference. The hourglass-shaped softwood pulp cores had the following dimensions: length: 15.5 in. (about 40 cm), width at the ears: 10.5 in. (about 27 cm), and width in the center: 3.75 in. (about 9.5 cm).

Absorbent structures of the present invention were made with softwood fibers and acrylic acid grafted starch hydrogel having a weight average particle size of about 25 microns ("Sanwet 1M 1000", from Sanyo Co., Japan) in a fiber:hydrogel ratio of 85:15, using the process of Example I. The absorbent structures had a basis weight of 0.12 g/in. (0.019 g/cm$^2$) and a caliper of 0.03 in. (0.076 cm), which corresponds to a density of 0.25 g/cm$^3$. The structures were covered with a sheet of envelope tissue, and cut to a size of 3.5 in.×15.5 in. (about 9×40 cm). The structures were inserted lengthwise into the above-described diapers, in between the hourglass-shaped core and the polyethylene backing sheet, the envelope tissue against the hourglass-shaped core.

Additional diapers were prepared by the same method, except that the dimensions of the absorbent structure insert were 2.25×15.5 in. (about 6×40 cm).

The inserts greatly increased the absorbent capacity for urine of the diapers.

EXAMPLE XII

A soft wood fiber drylap as obtained from a conventional paper making process was sprayed with a 10% solution of a quaternary ammonium compound of the formula

TABLE IX

| SAMPLE | A | B | C | D | E | F | G | H | I | J |
|---|---|---|---|---|---|---|---|---|---|---|
| Absorbent Core (g) | (35.6) | (25.0) | (25.0) | (25.0) | (18.0) | (21.0) | (35.6) | (18.0) | (35.6) | (15.0) |
| Fiber (g) | 34.9 | 19.7 | 20.6 | 19.8 | 14.8 | 17.7 | 35.6 | 15.3 | 35.6 | 12.3 |
| Hydrogel (g) | — | 4.9 | 4.5 | 4.3 | 3.3 | 3.1 | — | 3.3 | — | 2.7 |
| Tissue (g) | 6.0 | 6.0 | 6.0 | 6.0 | 6.0 | 6.0 | 6.0 | 6.0 | 6.0 | 6.0 |
| Total absorbent mat. | 40.9 | 30.6 | 31.1 | 30.1 | 24.1 | 26.8 | 41.6 | 24.6 | 41.6 | 21.0 |
| Fiber/hydrogel ratio | — | 80/20 | 82/18 | 82/18 | 82/18 | 85/15 | — | 82/18 | — | 82/18 |
| Grams of fluid to grade 3 leakage | 194 | 238 | 263 | 208 | 245 | 244 | 179 | 230 | 181 | 183 |
| Total Abs. X to leak | 4.7 | 7.8 | 8.4 | 6.9 | 10.2 | 9.1 | 4.3 | 9.4 | 4.4 | 8.7 |
| Core (less tissue) X to failure (g/g) | 5.1 | 9.0 | 9.9 | 8.0 | 12.7 | 11.0 | 4.6 | 11.6 | 4.7 | 11.2 |
| Core thickness (mm) | 2.9 | 0.7 | 0.7 | 0.7 | 0.5 | 0.6 | 2.9 | 0.5 | 2.9 | 0.4 |
| Core basis weight (mg/cm$^2$) | 29 | 20 | 20 | 20 | 15 | 17 | 29 | 15 | 29 | 12 |

Alternatively, one may reduce the bulk of the diaper core by less than a factor 7, (e.g. by a factor 4, samples B, C and D; by a factor 5; sample F; or by a factor 6, samples E and H) and yet achieve a substantial gain in absorbent capacity as compared to conventional disposable diapers.

EXAMPLE X

A diaper is prepared as described in U.S. Pat. No. 3,860,003, Buell, issued Jan. 14, 1975, incorporated herein by reference, except that, in addition to the absorbent body dislcosed therein (e.g., made from air-laid wood pulp) there is inserted between said absorbent body and the backsheet an hourglass-shaped absorbent structure of the present invention. The absorbent structure is made as described in Example I. The basis weight is 0.035 g/cm$^2$; the density is 0.3 g/cm$^3$, resulting in a thickness of 1.17 mm.

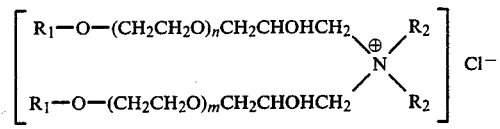

wherein n and m are integers from 2 to 10, $R_1$ is alkylaryl, and $R_2$ is alkyl having from 1 to 6 carbon atoms (Berocell 579, from Berol Chemicals, Inc., Metarie, LA).

The drylap was sprayed at a rate of 10 g solution per kg dry fiber, corresponding to 0.1% quaternary ammonium compound on the fiber. The drylap was then disintegrated, and the fibers mixed with an acrylic acid grafted starch hydrogel having a weight average particle size of about 250 microns ("Sanwet 1M 1000", from Sanyo Co., Ltd., Japan) in a fiber:hydrogel ratio of 80:20.

The fiber:hydrogel mixture was formed into an air-laid web having a basis weight of 0.13 g/in$^2$ (about 200 g/m$^2$). The web was calendered to a density of about 0.2 g/cm$^2$, corresponding to a thickness of about 0.038 in (about 2 mm). The absorbent structure thus obtained had excellent absorbent properties and softness. Similar structures are prepared, replacing the quaternary ammonium compound with nonionic and anionic softening agents. Structures having substantially similar properties are obtained.

The web containing the quaternary ammonium compound was cut into pads of 11⅝×16 in (about 30×41 cm). The pads were used in the manufacture of disposable diapers as described in Example VII.

What is claimed is:

1. A flexible, substantially unbonded, absorbent structure comprising an air-laid, substantially dry mixture of hydrophilic fibers and discrete particles of a water-insoluble, cross-linked polymeric hydrogel, in a fiber/hydrogel weight ratio from about 30:70 to about 98:2; said absorbent structure having a density of from about 0.15 to about 1 g/cm$^3$, a moisture content of less than about 10% by weight of the dry absorbent structure and a Gurley Stiffness value of less than 2 grams.

2. An absorbent structure according to claim 1, having a fiber/hydrogel weight ratio of from about 50:50 to about 95:5.

3. An absorbent structure according to claim 1, having a fiber/hydrogel weight ratio of from about 75:25 to about 90:10.

4. An absorbent structure according to claim 1, having a density of from about 0.15 to about 0.6 g/cm$^3$.

5. An absorbent structure according to claim 1, having a density of from about 0.25 to about 0.44 g/cm$^3$.

6. An absorbent structure according to claim 1 wherein the hydrophilic fibers are wood pulp fibers.

7. An absorbent structure according to claim 1, further comprising from about 0.01% to about 0.5% by weight of the hydrophilic fibers of a quaternary ammonium compound of the formula $$\left[ \begin{array}{c} R_1-O-(C_2H_4O)_n-CH_2-CHOH-CH_2 \\ R_2-O-(C_2H_4O)_m-CH_2-CHOH-CH_2 \end{array} \underset{N}{\overset{\oplus}{\diagup\diagdown}} \begin{array}{c} R_3 \\ R_4 \end{array} \right] X^\ominus$$

wherein $R_1$ and $R_2$ are hydrocarbyl groups containing from about 8 to about 22 carbon atoms, $R_3$ and $R_4$ are alkyl having from 1 to 6 carbon atoms; n and m are integers from 2 to about 10, and X is halogen.

8. An absorbent structure according to claim 1 which the has a Gurley Stiffness value of less than 1 g.

9. An absorbent structure according to claim 1, wherein the hydrogel particles have an average particle size of from about 30 microns to about 4 mm.

10. An absorbent structure according to claim 1, wherein the hydrogel particles have an average particle size of from about 50 microns to about 1 mm.

11. A flexible, substantially unbonded, absorbent structure comprising an air-laid, substantially dry mixture of wood pulp fibers and discrete particles of a water-insoluble, cross-linked polymeric hydrogel in a fiber/hydrogel weight ratio of from about 75:25 to about 90:10, said cross-linked polymeric hydrogel being selected from the group consisting of hydrolyzed acrylonitrile grafted starch, acrylic acid grafted starch, polyacrylate, co-polymers of isobutylene and maleic anhydride, and mixtures thereof, said particles having an average particle size of from about 50 microns to about 1 mm; said structure having a density of from about 0.15 to about 0.6 g/cm$^3$ and a Gurley Stiffness value of less than 2 grams.

12. A process for making a continuous, flexible absorbent structure, comprising the following steps:
   (a) air-laying into a web a dry mixture of hydrophilic fibers and particles of a water-insoluble, cross-linked polymeric hydrogel, said mixture having a fiber/hydrogel weight ratio of from about 30:70 to about 98:2 and a moisture content of less than about 10% by weight of the mixture; and,
   (b) compressing the web to a density of from about 0.15 to about 1 g/cm$^3$ and a Gurley Stiffness value of less than 2 grams.

13. A process according to claim 12, whereby the mixture of hydrophilic fibers and hydrogel particles has a fiber/hydrogel weight ratio of from about 50:50 to about 95:5.

14. A process according to claim 12, whereby the mixture of hydrophilic fibers and hydrogel particles has a fiber/hydrogel weight ratio of from about 75:25 to about 90:10.

15. A process according to claim 12 whereby the web is compressed to a density of from about 0.15 to about 0.6 g/cm$^3$.

16. A process according to claim 12 whereby the web is compressed to a density of from about 0.25 to about 0.4 g/cm$^3$.

17. A process according to claim 12, wherein the hydrophilic fibers are wood pulp fibers.

18. A process according to claim 12, wherein the cross-linked polymeric hydrogel is selected from the group consisting of hydrolyzed acrylonitrile grafted starch, acrylic acid grafted starch, polyacrylates, co-polymers of isobutylene and maleic anhydride, and mixtures thereof.

19. A process according to claim 12, wherein the hydrogel particles have an average particle size of from about 30 microns to about 4 mm.

20. A process according to claim 12 wherein the hydrogel particles have an average particle size of from about 50 microns to about 1 mm.

21. A process for making a flexible, substantially unbonded, absorbent structure, comprising the following steps:
   (a) dry mixing of hydrophilic fibers and particles of a water-insoluble, cross-linked polymeric hydrogel in a weight ratio of from about 75:25 to about 90:10, said particles having an average size of from about 50 microns to about 1 mm, and said cross-linked polymeric hydrogel being selected from the group consisting of hydrolyzed acrylonitrile grafted starch, acrylic acid grafted starch, polyacrylates, copolymers of isobutylene and maleic anhydride, and mixtures thereof to form a fiber/hydrogel mixture having a moisture content of less than 10% by weight;
   (b) air-laying of the mixture obtained in step (a) into a web; and
   (c) compressing the web into a density of from about 0.15 to about 0.6 g/cm$^3$ and a Gurley Stiffness value of less than 2 grams.

22. An absorbent structure made according to the process of claim 12.

23. An absorbent product comprising the absorbent structure of claim 1.

24. A disposable diaper, comprising:
(a) a liquid impervious backing sheet;
(b) a hydrophobic top sheet;
(c) an absorbent structure according to claim 1, said structure being placed between the backing sheet and the top sheet.

25. A disposable diaper, comprising:
(a) a liquid impervious backing sheet;
(b) a hydrophobic topsheet; and
(c) an absorbent structure according to claim 7, said structure being placed between the backing sheet and the topsheet.

26. A disposable diaper according to claim 24, wherein the absorbent structure has a basis weight of from about 0.01 to about 0.05 g/cm$^2$.

27. A disposable diaper according to claim 24 wherein the absorbent structure is wrapped in envelope tissue.

28. A disposable diaper according to claim 27 wherein the absorbent structure has a thickness of from about 0.3 mm to about 2 mm.

29. A disposable diaper according to claim 27 wherein the absorbent structure has a thickness of from about 0.5 mm to about 1 mm.

30. A disposable diaper according to claim 24 wherein the absorbent structure is hourglass-shaped.

31. A disposable diaper according to claim 24 further comprising a wood pulp fiber absorbent core which is placed between the hydrophobic top sheet (b) and the absorbent structure (c).

32. A disposable diaper according to claim 31 wherein the wood pulp fiber absorbent core is hourglass shaped and the absorbent structure (c) is rectangular.

33. A sanitary napkin comprising:
(a) a liquid impervious backing sheet;
(b) a hydrophobic top sheet;
(c) an absorbent structure according to claim 1, said structure being placed between the backing sheet and the top sheet.

* * * * *

UNITED STATES PATENT AND TRADEMARK OFFICE
CERTIFICATE OF CORRECTION

PATENT NO. : 4,610,678

DATED : September 9, 1986

INVENTOR(S) : Paul T. Weisman and Stephen A. Goldman

It is certified that error appears in the above-identified patent and that said Letters Patent are hereby corrected as shown below:

On the cover page, the assignee should be identified as follows:
--Assignee: The Procter & Gamble Company, Cincinnati, Ohio--.

On the cover page, in the "Related U.S. Application Data" section;
delete "Ser. No. 437,846" and insert therefor --Ser. No. 473,846--.

Column 1, line 7; delete "Ser. No. 437,846" and insert therefor
--Ser. No. 473,846--

Column 19, line 36, in Claim 5;
delete "0.44 g/cm$^3$" and insert therefor --0.4 g/cm$^3$--.

Column 19, line 55, in Claim 8;
delete "the".

Column 22, line 22; add the following additional Claim 34;
--34. An absorbent structure according to Claim 1 wherein the water-insoluble hydrogel is a cross-linked polymer selected from the group consisting of hydrolyzed acrylonitrile grafted starch, acrylic acid

UNITED STATES PATENT AND TRADEMARK OFFICE
CERTIFICATE OF CORRECTION

PATENT NO. : 4,610,678
DATED : September 9, 1986
INVENTOR(S) : Paul T. Weisman and Stephen A. Goldman It is certified that error appears in the above-identified patent and that said Letters Patent is hereby corrected as shown below:

grafted starch, polyacrylates, copolymers of isobutylene and maleic anhydride, and mixtures thereof.--.

Signed and Sealed this

Second Day of August, 1988

Attest:

DONALD J. QUIGG

*Attesting Officer*    *Commissioner of Patents and Trademarks*